(12) United States Patent
Schurman et al.

(10) Patent No.: US 8,788,003 B2
(45) Date of Patent: Jul. 22, 2014

(54) MONITORING BLOOD CONSTITUENT LEVELS IN BIOLOGICAL TISSUE

(75) Inventors: Matthew J. Schurman, Somerset, NJ (US); Walter J. Shakespeare, Macungie, PA (US)

(73) Assignee: GLT Acquisition Corp., Irvine, CA (US)

( * ) Notice: Subject to any disclaimer, the term of this patent is extended or adjusted under 35 U.S.C. 154(b) by 43 days.

(21) Appl. No.: 13/456,137

(22) Filed: Apr. 25, 2012

(65) Prior Publication Data

US 2012/0209094 A1 Aug. 16, 2012

Related U.S. Application Data

(63) Continuation of application No. 11/832,721, filed on Aug. 2, 2007, now Pat. No. 8,204,566, which is a continuation of application No. 10/916,236, filed on Aug. 11, 2004, now Pat. No. 7,254,429.

(51) Int. Cl.
*A61B 5/1455* (2006.01)

(52) U.S. Cl.
USPC .......................................... 600/316; 600/322

(58) Field of Classification Search
USPC ........................... 600/310, 316, 322, 473, 476
See application file for complete search history.

(56) References Cited

U.S. PATENT DOCUMENTS

| 3,826,905 A | 7/1974 | Valkama et al. |
| 3,958,560 A | 5/1976 | March |
| 4,014,321 A | 3/1977 | March |
| 4,476,875 A | 10/1984 | Nilsson et al. |
| 4,590,948 A | 5/1986 | Nilsson |
| 4,606,351 A | 8/1986 | Lubbers |
| 4,655,225 A | 4/1987 | Dahne et al. |

(Continued)

FOREIGN PATENT DOCUMENTS

| EP | 0282234 | 9/1988 |
| EP | 0160768 | 5/1989 |

(Continued)

OTHER PUBLICATIONS

Arnold. M.A. et al., "Determination of Physiological Levels of Glucose in an Aqueous Matrix with Digitally Filtered Fourier Transform Near-Infrared Spectra," Anal. Chem. 64(14):1457-64 (1990).

(Continued)

*Primary Examiner* — Eric Winakur
(74) *Attorney, Agent, or Firm* — Knobbe, Martens, Olson & Bear, LLP

(57) ABSTRACT

In accordance with the invention, a low coherence interferometer is used to non-invasively monitor the concentration of glucose in blood by shining a light over a surface area of human or animal tissue, continuously scanning the light over a two dimensional area of the surface, collecting the reflected light from within the tissue and constructively interfering this reflected light with light reflected along a reference path to scan the tissue in depth. Since the reflection spectrum is sensitive to glucose concentration at particular wavelengths, measurement and analysis of the reflected light provides a measure of the level of glucose in the blood. The measurement of glucose is taken from multiple depths within blood-profused tissue, and sensitivity is preferably enhanced by the use of multiple wavelengths. Noise or speckle associated with this technique is minimized by continuously scanning the illuminated tissue in area and depth.

22 Claims, 4 Drawing Sheets

(56) References Cited

U.S. PATENT DOCUMENTS

| | | |
|---|---|---|
| 4,704,029 A | 11/1987 | Van Heuvelen |
| 4,731,363 A | 3/1988 | Hamilton et al. |
| 4,743,604 A | 5/1988 | Alig et al. |
| 4,750,830 A | 6/1988 | Lee |
| 4,834,111 A | 5/1989 | Khanna et al. |
| 4,871,755 A | 10/1989 | Alig et al. |
| 4,873,989 A | 10/1989 | Einzig |
| 4,882,492 A | 11/1989 | Schlager |
| 4,883,953 A | 11/1989 | Koashi et al. |
| 4,890,621 A | 1/1990 | Hakky et al. |
| 4,901,728 A | 2/1990 | Hutchison |
| 4,948,248 A | 8/1990 | Lehman |
| 4,960,128 A | 10/1990 | Gordon et al. |
| 4,964,408 A | 10/1990 | Hink et al. |
| 4,979,509 A | 12/1990 | Hakky |
| 4,989,978 A | 2/1991 | Groner |
| 5,025,785 A | 6/1991 | Weiss |
| 5,028,787 A | 7/1991 | Rosenthal et al. |
| 5,041,187 A | 8/1991 | Hink et al. |
| 5,054,487 A | 10/1991 | Clarke |
| 5,069,213 A | 12/1991 | Polczynski |
| 5,070,874 A | 12/1991 | Barnes et al. |
| 5,101,814 A | 4/1992 | Palti |
| 5,112,124 A | 5/1992 | Harjunmaa et al. |
| 5,115,133 A | 5/1992 | Knudson |
| 5,163,438 A | 11/1992 | Gordon et al. |
| 5,168,325 A | 12/1992 | Yoder-Short |
| 5,178,153 A | 1/1993 | Einzig |
| 5,209,231 A | 5/1993 | Cote et al. |
| 5,222,495 A | 6/1993 | Clarke et al. |
| 5,222,496 A | 6/1993 | Clarke et al. |
| 5,243,983 A | 9/1993 | Tarr et al. |
| 5,267,152 A | 11/1993 | Yang et al. |
| 5,277,181 A | 1/1994 | Mendelson et al. |
| 5,278,627 A | 1/1994 | Aoyagi et al. |
| 5,313,941 A | 5/1994 | Braig et al. |
| 5,319,355 A | 6/1994 | Russek |
| 5,321,501 A | 6/1994 | Swanson et al. |
| 5,337,744 A | 8/1994 | Branigan |
| 5,341,805 A | 8/1994 | Stavridi et al. |
| 5,348,003 A | 9/1994 | Caro |
| 5,349,953 A | 9/1994 | McCarthy et al. |
| 5,361,758 A | 11/1994 | Hall et al. |
| D353,195 S | 12/1994 | Savage et al. |
| D353,196 S | 12/1994 | Savage et al. |
| 5,370,114 A | 12/1994 | Wong et al. |
| 5,372,136 A | 12/1994 | Steuer et al. |
| 5,376,336 A | 12/1994 | Lubbers et al. |
| 5,377,676 A | 1/1995 | Vari et al. |
| 5,379,238 A | 1/1995 | Stark |
| 5,383,452 A | 1/1995 | Buchert |
| 5,398,681 A | 3/1995 | Kupershmidt |
| D359,546 S | 6/1995 | Savage et al. |
| 5,431,170 A | 7/1995 | Mathews |
| 5,433,197 A | 7/1995 | Stark |
| 5,435,309 A | 7/1995 | Thomas et al. |
| D361,840 S | 8/1995 | Savage et al. |
| D362,063 S | 9/1995 | Savage et al. |
| 5,448,992 A | 9/1995 | Kupershmidt |
| 5,452,716 A | 9/1995 | Clift |
| 5,452,717 A | 9/1995 | Branigan et al. |
| D363,120 S | 10/1995 | Savage et al. |
| 5,456,252 A | 10/1995 | Vari et al. |
| 5,457,535 A | 10/1995 | Schmidtke et al. |
| 5,459,570 A | 10/1995 | Swanson et al. |
| 5,479,934 A | 1/1996 | Imran |
| 5,482,036 A | 1/1996 | Diab et al. |
| 5,490,505 A | 2/1996 | Diab et al. |
| 5,492,118 A | 2/1996 | Gratton et al. |
| 5,494,043 A | 2/1996 | O'Sullivan et al. |
| 5,501,226 A | 3/1996 | Petersen et al. |
| 5,533,511 A | 7/1996 | Kaspari et al. |
| 5,534,851 A | 7/1996 | Russek |
| 5,535,743 A | 7/1996 | Backhaus et al. |
| 5,549,114 A | 8/1996 | Petersen et al. |
| 5,551,422 A | 9/1996 | Simonsen et al. |
| 5,553,616 A | 9/1996 | Ham et al. |
| 5,561,275 A | 10/1996 | Savage et al. |
| 5,562,002 A | 10/1996 | Lalin |
| 5,582,168 A | 12/1996 | Samuels et al. |
| 5,582,171 A | 12/1996 | Chornenky et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,710,630 A | 1/1998 | Essenpreis et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,795,295 A | 8/1998 | Hellmuth et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,036,919 A | 3/2000 | Thym et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,147,108 A | 11/2000 | Hauptman |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,294,062 B1 | 9/2001 | Buck, Jr. et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |

(56) References Cited

U.S. PATENT DOCUMENTS

| | | |
|---|---|---|
| 6,397,091 B2 | 5/2002 | Diab et al. |
| 6,425,863 B1 | 7/2002 | Werner et al. |
| 6,430,437 B1 | 8/2002 | Marro |
| 6,430,525 B1 | 8/2002 | Weber et al. |
| 6,443,881 B1 | 9/2002 | Finger |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,216 B1 | 4/2003 | Wilsey et al. |
| 6,541,756 B2 | 4/2003 | Schulz et al. |
| 6,542,764 B1 | 4/2003 | Al-Ali et al. |
| 6,544,212 B2 | 4/2003 | Galley et al. |
| 6,556,853 B1 | 4/2003 | Cabib et al. |
| 6,572,566 B2 | 6/2003 | Effenhauser |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,554 B1 | 3/2004 | Miltner et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,073 B1 | 4/2004 | Motamedi et al. |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,780,651 B2 | 8/2004 | Douglas et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,337 B2 | 12/2004 | Cornsweet |
| 6,837,337 B2 | 1/2005 | Thomas et al. |
| 6,847,449 B2 | 1/2005 | Bashkansky et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,280,860 B2 | 10/2007 | Ikeda et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,734 B2 | 12/2007 | Dogariu |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,353,055 B2 * | 4/2008 | Hogan .................. 600/316 |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |

(56) References Cited

U.S. PATENT DOCUMENTS

| | | |
|---|---|---|
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,884,945 B2 | 2/2011 | Srinivasan et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,547,209 B2 | 10/2013 | Kiani et al. |
| 8,548,548 B2 | 10/2013 | Al-Ali et al. |
| 8,548,550 B2 | 10/2013 | Al-Ali |
| 2002/0016533 A1 | 2/2002 | Marchitto et al. |
| 2004/0260158 A1 | 12/2004 | Hogan |
| 2005/0043597 A1 | 2/2005 | Xie |
| 2005/0070771 A1 | 3/2005 | Rule et al. |
| 2005/0101846 A1 | 5/2005 | Fine et al. |
| 2005/0105097 A1 | 5/2005 | Fang-Yen et al. |
| 2005/0226912 A1 | 10/2005 | Lowery |
| 2005/0254061 A1 | 11/2005 | Alphonse |
| 2008/0021293 A1 | 1/2008 | Schurman et al. |
| 2011/0015505 A1 | 1/2011 | Schurman et al. |
| 2011/0319731 A1 | 12/2011 | Schurman et al. |

FOREIGN PATENT DOCUMENTS

| | | |
|---|---|---|
| EP | 0127947 | 8/1990 |
| EP | 0280986 | 7/1992 |
| EP | 0317121 | 2/1994 |

(56) References Cited

FOREIGN PATENT DOCUMENTS

| | | |
|---|---|---|
| EP | 0536187 | 9/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |
| WO | WO 95/32416 | 11/1995 |
| WO | WO 02/065090 | 8/2002 |

OTHER PUBLICATIONS

Arnold, V.W. et al., "Fourier Transformation Infrared Spectrometry—A New (Old) Method of Detection in Forensic Chemistry and Criminal Investigation," Beitr Gerichtl Med. 47:123-47 (1989).
Bruulsema, J.T. et al., "Correlation Between Blood Glucose Concentration in Diabetics and Noninvasively Measured Tissue Optical Scattering Coefficient," Opt. Lett. 22(3):190-93 (1997).
Burritt, M.F., "Current Analytical Approaches to Measuring Blood Analytes," Clin. Chem. 36(8 pt.2):1562-66 (1990).
Chira, I.S. et al., "Light Scattering by Blood Components After Supplying Glucose," Biomed. Tech. 35(5): 102-06 (1990).
Christison, G.B. et al., "Laser Photoacoustic Determination of Physiological Glucose Concentrations in Human Whole Blood," Med. Biol. Eng. Comput. 31(3):284-90 (1993).
Cote, G.L. et al., "Noninvasive Optical Polarimetric Glucose Sensing Using a True Phase Measurement Technique," IEEE Trans. Biomed. Enq, 39(7):752-56 (1992).
CRC Press, "Handbook of Chemistry and Physics" 64th ed. pp. D-223, D-224, and D. 235.
Drezek, R. et al., "Light Scattering From Cell: Finite Difference Time-Domain Simulations and Goniometric Measurements," Appl. Opt. 38(16):3651-61 (1999).
Duck, F.A., Physical Properties of Tissue, (Academic London 1990).
Dyer, D.G. et al., "Accumulation of Maillard Reaction Products in Skin Collagen in Diabetes and Aging," J. Clin. Invest. 91:2463-69 (1993).
Esenaliev, R.O, et al., "Noninvasive Monitoring of Glucose Concentration with Optical Coherence Tomography," Optics Lett. 26(13):992-94 (2001).
Faber, D.J. et al., "Light Absorption of (oxy-)Hemoglobin Assessed by Spectroscopic Optical Coherence Tomography," Optics Lett. 28(16):1436-38 (2003).
Fercher, A. et al., "In Vivo Optical Coherence Tomography," Amer, J. Opthalmol, 116(1):113-14 (1993).
Flock, S.T. et al., "Total Attenuation Coefficients and Scattering Phase Functions of Tissues and Phantom Materials at 633 nm," Med. Phvs. 14(5):835-41 (1987).
Fogt, E.J., "Continuous Ex Vivo and In Vivo Monitoring with Chemical Sensors," Clin. Chem. 36(8 pt.2):1573-80 (1990).
Frank, K.H. et al., "Measurements of Angular Distributions of Rayleigh and Mie Scattering Events in Biological Models," Phvs. Med. Biol. 34(8):1901-16 (1989).
Gabriel Y.I. et al., "Transcutaneous Glucose Measurement Using Near-Infrared Spectroscopy During Hypoglycemia," Diabetes Care 22(12):2026-32 (1999).
Galanzha, E.I. et al., "Skin Backreflectance and Microvascular System Functioning at the Action of Osmotic Agents," J, Phvs. D. Appl. Phvs. 36:1739-46 (2003).
Gilbert, J.W. et al., "A Cerebrospinal Fluid Glucose Biosensor for Diabetes Mellitus," ASAIO J. 38(2):82-87 (1992).

Goetz, M.J. et al., "Application of a Multivariate Technique to Raman Spectra for Quantification of Body Chemicals," IEEE Trans, Biomed. Eng, 42:728-31 (1995).
Goodman, J.W., Some Fundamental Properties of Speckle, J. Optical Soc. of America 66(11):1145-50 (1976).
Gough, D.A., "The Composition and Optical Rotary Dispersion of Bovine Aqueous Humor," Diabetes Care 5(3):266-70 (1982).
Gunby, P., "Laser-Implant Contact Lens Could be Glucose Monitor," JAMA 243(4):317 (1980).
Guyton, A.C., Textbook of medical physiology, (W.B. Saunders Company 1992).
Huang, D, et al., "Optical Coherence Tomograph," Science 254:1178-81 (1991).
Huang, Y.L. et al., "On-Line Determination of Glucose Concentration Throughout Animal Cell Cultures Based on Chemiluminescent Detection of Hydrogen Peroxide Coupled with Flow-Injection Analysis," J. Biotechnol. 18(1-2):161-72 (1991).
International Search Report from PCT/US05/26744, mailed Oct. 25, 2006.
International Search Report, from corresponding PCT/US06/13775, mailed Sep. 13, 2006.
International Search Report, from corresponding PCT/US06/21535, mailed Feb. 21, 2008.
Kaiser, N., "Laser Absorption Spectroscopy with an ATR Prism—Noninvasive in Vivo Determination of Glucose," Horm. Metab. Res. Suppl. 8:30-33 (1979).
Kajiwara, K. et al., "Spectroscopic Quantitative Analysis of Blood Glucose by Fourier Transform Infrared Spectroscopy with an Attenuated Total Reflection Prism," Med, Prog. Technol. 18(3):181-89 (1992).
Khalil, O.S. "Spectroscopic and Clinical Aspects of Noninvasive Glucose Measurements," Clin. Chern. 45(2):165-77 (1999).
Kholodnykh, A.I. et al., "Precision of Measurement of Tissue Optical Properties with Optical Coherence Tomography," Appl. Optics 42(16):3027-37 (2003).
King, T.W. et al., "Multispectral Polarimetric Glucose Detection Using a Single Pockels Cell," Optical Engineering 33(8):2746-53 (1994).
Kohl, M. et al., "The Influence of Glucose Concentration Upon the Transport of Light in Tissue-Simulating Phantoms," Phys. Med. Biol. 40:1267-87(1995).
Kohl, M. et al., "Influence of Glucose Concentration on Light Scattering in Tissue-Simulating Phantoms," Optics Letters 19(24):2170-72 (1994).
Kruse-Jarres, J.D., "Physicochemical Determinations of Glucose in Vivo," J. Clin. Chem. Clin. Biochem. 26(4):201-08 (1988).
Larin, K.V. et al., "Optoacoustic Signal Profiles for Monitoring Glucose Concentration in Turbid Media," SPIE Proc. 3726:576-83 (1988).
Larin, K.V. et al., "Noninvasive Blood Glucose Monitoring With Optical CoherenceTomography," Diabetes Care 25(12):2263-67 (2002).
Larin, K.V. et al., "Specificity of Noninvasive Blood Glucose Sensing Using Optical Coherence Tomography Technique: A Pilot Study," Physics in Med. & Biol. 48:1371-90 (2003).
Larin, K.V. et al., "Phase-Sensitive Optical Low-Coherence Reflectometry for the Detection of Analyte Concentrations," Appl. Optics 43(17):3408-14 (2004).
Lide, D.R., CRC Handbook of Chemistry and Physics, $79^{th}$ ed. (CRC Press, Boca Raton, Florida, 1998).
MacKenzie, H.A. et al., "Advances in Photoacoustic Noninvasive Glucose Testing," Clin. Chem. 45(9):1587-95 (1999).
Maier, J.S. et al., "Possible Correlation Between Blood Glucose Concentration and the Reduced Scattering Coefficient of Tissues in the Near Infrared," Optics Lett. 19(24):2062-64 (1994).
March, W. et al., "Optical Monitor of Glucose," Trans. Am. Soc. Artlf. Intern. Organs 25:28-31 (1979).
March, W.F. et al., "Noninvasive Glucose Monitoring of the Aqueous Humor of the Eye: Part II. Animal Studies and the Scleral Lens," Diabetes Care 5(3):259-65 (1982).
Mendelson, Y. et al., "Blood Glucose Measurement by Multiple Attenuated Total Reflection and Infrared Absorption Spectroscopy," IEEE Trans. Biomed. Eng. 37(5):458-65 (1990).

(56) References Cited

OTHER PUBLICATIONS

Moreno-Bondi, M,C. et al., "Oxygen Optrode for Use in a Fiber-Optic Glucose Biosensor," Anal. Chem. 62(21):2377-80 (1990).

Muller, A., "In Vivo Measurement of Glucose Concentration with Lasers," Harm. Metab. Res. Suppl. 8:33-35 (1979).

Narayanaswamy, R., "Current Developments in Optical Biochemical Sensors," Biosens. Bioelectron. 6(6):467-75 (1991).

Pan, S. et al., "Near-Infrared Spectroscopic Measurement of Physiological Glucose Levels in Variable Matrices of Protein and Triglycerides," Anal, Chem. 68:1124-35 (1996).

Peterson, J.I. et al., "A Miniature Fiberoptic pH Sensor Potentially Suitable for Glucose Measurements," Diabetes Care 5(3):272-74 (1982).

Quan, K.M. et al., "Glucose Determination by a Pulsed Photoacoustic Technique—An Experimental Study Using a Gelatin-Based Tissue Phantom," Phys. Med. Biol. 38(12): 1911-22 (1993).

Rabinovitch, B. et al., "Noninvasive Glucose Monitoring of the Aqueous Humor of the Eye: Part I. Measurement of Very Small Optical Rotations," Diabetes Care 5(3):254-58 (1982).

Robinson, M.R. et al., "Noninvasive Glucose Monitoring in Diabetic Patients: A Preliminary Evaluation," Clin. Chem. 38(9):1618-22 (1992).

Robinson, R.J, et al., "Glucose-Sensitive Membrane and Infrared Absorption Spectroscopy for Potential Use as an Implantable Glucose Sensor," ASAIO J. 38(3):M458-62 (1992).

Rusch, T.L. et al., "Signal Processing Methods for Pulse Oximetry," Comput. Biol. Med. 26(2):143-59 (1996).

Schmitt, J.M. et al., "Measurement of Optical Properties of Biological Tissues by Low-Coherence Reflectometrv," Appl. Optics 32(30):6032-42 (1993).

Schmitt, J.M. et al., "Optical Coherence Tomography (OCT): A Review," IEEE J. Selected Topics in Quantum Electronics 5(4):1205-15 (1999).

Schmitt, J.M. et al., "Speckle in Optical Coherence Tomography," J. Biomed. Optics 4(1):95-105 (1999).

Sevick, E.M. et al., "Near-Infrared Optical Imaging of Tissue Phantoms with Measurement in the Change of Optical Path Lengths," Adv. Exp. Med. Biol. 345:815-23 (1994).

Sodickson, L.A. et al., "Kromoscopic Analysis: A Possible Alternative to Spectroscopic Analysis for Noninvasive Measurement of Analytes in Vivo," Clin. Chern. 40(9):1838-44 (1994).

Star, W.M. et al., "Light Dosimetry: Status and Prospects," J. Photochem. Photobiol. 1(2):149-67 (1987).

Stoddart, S. et al., "Pulse Oximetry: What it is and How to Use it," J. Neonatal Nursing 10:12-14 (1997).

Takai, N. et al., "Studies of the Development of Optical Fiber Sensors for Biochemical Analysis," Artif. Organs 15{2):86-89 (1991).

Tunchin, V.V. et al., "Light Propagation in Tissues with Controlled Optical Properties," J. Biomed. Opt. 2(4):401-17 (1997).

Wang, L. et al., "Speckle Reduction in Laser Projection Systems by Diffractive Optical Elements," Appl. Optics 37(10):1770-75 (1998).

Weast, R.C., et al, CRC Handbook of Chemistry and Physics, $70^{th}$ ed., (CRC Cleveland, Ohio, 1989).

Welch, A.J. et al., Practical Models for Light Distribution in Laser-Irradiated Tissue,' Lasers Surq. Med. 6(6):488-93 (1987).

Wicksted, J.P. et al., "Monitoring of Aqueous Humor Metabolites Using Raman Spectroscopy," SPIE Proc. 2135:264-74 (1994).

Zeller, H. et al., Blood Glucose Measurement by Infrared Spectroscopy,—J. Artif. Organs 12(2):129-35 (1989).

Zhao, Yonghua, et al. "Doppler standard deviation imaging for clinical monitoring of in vitro human skin blood flow." Optics Letters. Sep. 15, 2000. vol. 25, No. 18 pp. 1358-1360.

* cited by examiner

MONITORING BLOOD CONSTITUENT LEVELS IN BIOLOGICAL TISSUE

CROSS-REFERENCE TO RELATED APPLICATIONS

The present application is a continuation application of U.S. application Ser. No. 11/832,721, filed Aug. 2, 2007, entitled "Method and Apparatus for Monitoring Blood Constituent Levels in Biological Tissue," which is a continuation of U.S. application Ser. No. 10/916,236, filed on Aug. 11, 2004, entitled "Method and Apparatus for Monitoring Glucose Levels in a Biological Tissue," now U.S. Pat. No. 7,254,429, the entire contents of which are hereby incorporated by reference in their entirety.

BACKGROUND

1. Field of the Invention

This invention pertains to methods and apparatus for monitoring the blood glucose level in biological tissues. It is especially useful for non-invasive monitoring of blood glucose in human or animal diabetics. Specifically, it relates to methods and apparatus for non-invasive monitoring of blood glucose using optical coherence interferometry with continuous area scanning and simultaneous depth scanning to reduce the effect of speckle (noise).

2. Description of the Related Art

Monitoring of blood glucose (blood sugar) concentration levels has long been critical to the treatment of diabetes in humans. Current blood glucose monitors involve a chemical reaction between blood serum and a test strip, requiring an invasive extraction of blood via a lancet or pinprick. Small handheld monitors have been developed to enable a patient to perform this procedure anywhere, at any time. But the inconvenience of this procedure—specifically the blood extraction and the use and disposition of test strips—has led to a low level of compliance. Such low compliance can lead to serious medical complications. Thus, a non-invasive method for monitoring blood glucose is needed.

Studies have shown that optical methods can detect small changes in biological tissue scattering related to changes in levels of blood sugar. Although highly complex, a first order approximation of monochromatic light scattered by biological tissue can be described by the following simplified equation:

$$I_R = I_O \exp[-(\mu_a + \mu_s)L]$$

where $I_R$ is the intensity of light reflected from the skin, $I_O$ is the intensity of the light illuminating the skin, $\mu_a$ is the absorption coefficient of the skin at the specific wavelength of light, $\mu_s$ is the scatter coefficient of the skin at the specific wavelength of light, and L is the total path traversed by the light. From this relationship it can be seen that the intensity of the light decays exponentially as either the absorption or the scattering of the tissue increases.

It is well established that there is a difference in the index of refraction between blood serum/interstitial fluid (blood/IF) and membranes of cells such as blood cells and skin cells. (See, R. C. Weast, ed., *CRC Handbook of Chemistry and Physics*, 70th ed., (CRC Cleveland, Ohio 1989)). This difference can produce characteristic scattering of transmitted light. Glucose, in its varying forms, is a major constituent of blood/IF. The variation of glucose levels in blood/IF changes its refractive index and thus, the characteristic scattering from blood-perfused tissue. In the near infrared wavelength range (NIR), blood glucose changes the scattering coefficient more than it changes the absorption coefficient. Thus, the optical scattering of the blood/IF and cell mixture varies as the blood glucose level changes. Accordingly, an optical method has potential for non-invasive measurement of blood glucose concentration.

Non-invasive optical techniques being explored for blood glucose application include polarimetry, Raman spectroscopy, near-infrared absorption, scattering spectroscopy, photoacoustics and optoacoustics. Despite significant efforts, these techniques have shortcomings such as low sensitivity, low accuracy (less than current invasive home monitors) and insufficient specificity of glucose concentration measurement within the relevant physiological range (4-30 mM or 72-540 mg/dL). Accordingly, there is a need for an improved method to non-invasively monitor glucose.

Optical coherence tomography, or OCT, is an optical imaging technique using light waves that produces high resolution imagery of biological tissue. OCT creates its images by interferometrically scanning in depth a linear succession of spots, and measuring absorption and/or scattering at different depths in each successive spot. The data is then processed to present an image of the linear cross section. It has been proposed that OCT might be useful in measuring blood glucose.

There are, however, major drawbacks to the use of OCT for glucose monitoring. First, the OCT process requires lengthy scanning to reduce optical noise ("speckle"). Speckle arises from wavefront distortion, when coherent light scatters from tissue. OCT seeks to minimize speckle by averaging it out over many measurements. However this approach in OCT requires a time period impractically long for a home monitor, and even then speckle in OCT remains problematic for achieving a sufficiently accurate measurement of glucose level.

A second drawback of OCT is that it requires complex processing to form an image and even further processing to analyze the image data to determine glucose levels.

A third drawback is that OCT requires expensive, bulky, precision equipment neither suitable for transport or for use outside the laboratory. Accordingly, there is a need for an improved methods and apparatus for non-invasive blood glucose monitoring.

SUMMARY

In accordance with the invention, the blood glucose concentration within a biological tissue is monitored by providing light having scattering properties sensitive to the glucose concentration within the tissue and continuously scanning the light over a two dimensional area of the tissue while, at the same time, interferometrically scanning the tissue in depth. The light reflected from the scanned tissue is collected and analyzed to determine the concentration of glucose in the tissue. In an advantageous embodiment light from one or more sources is split into a sample beam and a reference beam. The sample beam is continuously scanned over the surface and the phase of the reference beam is varied and interfered with the reflected light to effect interferometric depth scanning. In a preferred embodiment, the light provided is composed of at least two different wavelengths having measurably different scattering properties for glucose-containing tissue or biological indicators of such tissue.

An apparatus for measuring the blood glucose level in biological tissue comprises one or more light sources to provide light. Optical fiber or lens-directed paths direct the light onto the tissue, an area scanner continuously scans the light over a two-dimensional area of the tissue and an interferometer effectively scans the tissue in depth. The interferometer also collects, analyzes and measures the light reflected within the tissue. A processor responsive to the light measurements then calculates the glucose level of blood-perfused regions of the tissue. Advantageously, the apparatus uses low coherence light sources (light emitting diodes (LEDs) or super luminescent diodes (SLEDs), a low coherence interferometer (LCI), and beam focusing optics. The continuous scanning over a two-dimensional area and the depth scanning reduce noise or speckle and optimize the amount of blood-perfused tissue scanned.

BRIEF DESCRIPTION OF THE DRAWINGS

The advantages, nature and various additional features of the invention will appear more fully upon consideration of the illustrative embodiments now to be described in detail in connection with the accompanying drawings. In the drawings.

It is to be understood that the drawings are for the purpose of illustrating the concepts of the invention, and except for the graphs, are not to scale.

DETAILED DESCRIPTION OF SPECIFIC EMBODIMENTS

Figure 1B:
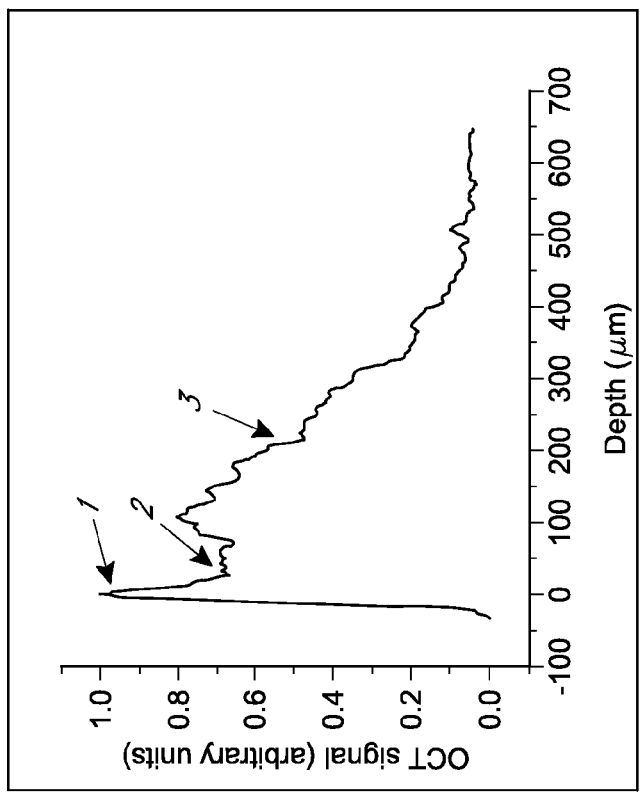
FIGS. 1a and 1b illustrate the anatomy of the skin and the resulting OCT signal.
Figure 1A:
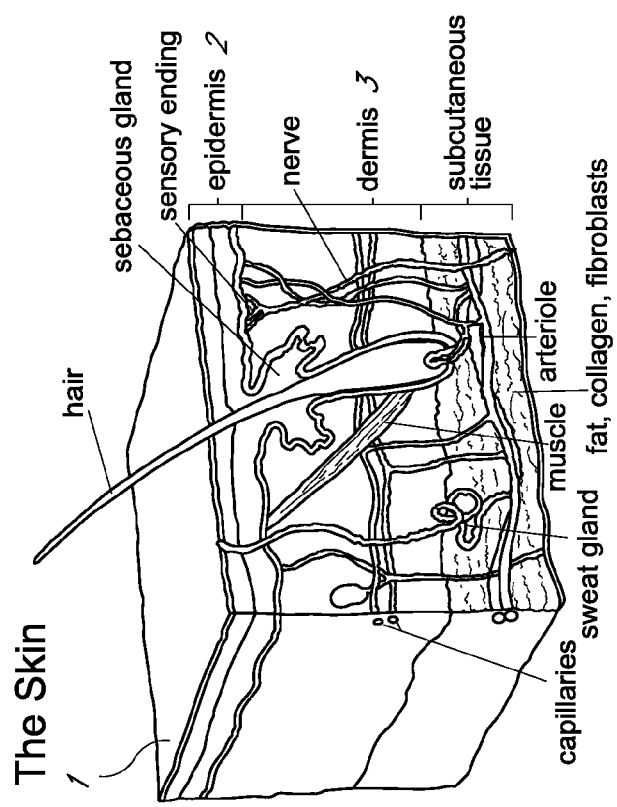

FIG. 1a is a schematic cross section of the skin showing the skin surface 1, the epidermis layer 2 and the dermis layer 3. Various additional structures are labeled. Some structures, such as hair and its associated follicles, scatter light in a manner unrelated to glucose concentration. Other regions, such as regions in the dermis near the capillaries are perfused with blood and IF blood-perfused tissues) and light scattered from these regions is highly correlated with glucose concentration.

FIG. 1b graphically illustrates light scattered within the skin as a function of depth. Region 1 of the curve corresponds to light reflected from the skin surface. Region 2 shows light scattered within the epidermis, and Region 3 is light scattered from the dermis. As we will show, slope of the curve at depths where the tissue is perfused with blood (e.g. near the capillaries) is highly correlated with blood glucose levels.

Figure 2A:
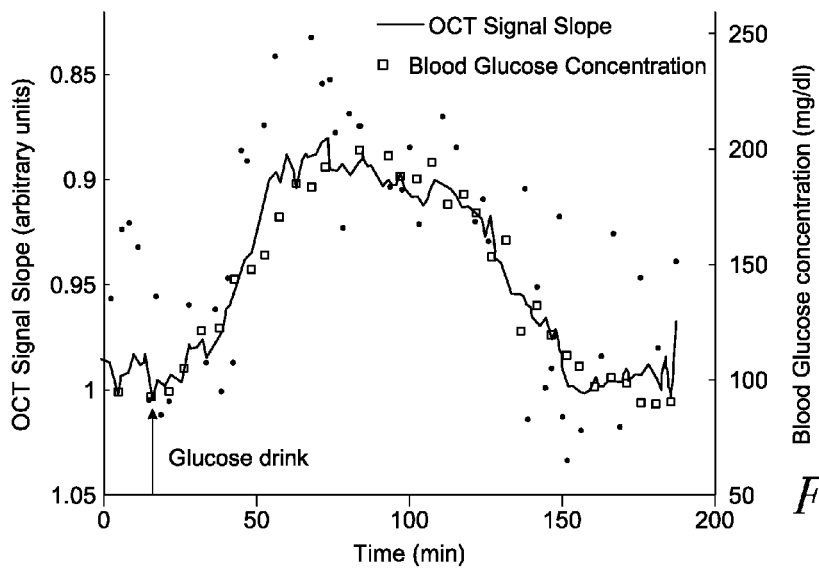
FIGS. 2a and 2b graphically represent the data collected from an OCT signal and blood measurements and the correlation between the two.

FIG. 2a graphically plots the slope of the optical signal reflected by blood-perfused tissue (the continuous line) and the measured blood glucose concentration (rectangular dots) as a function of time after a human subject ingests a glucose drink. As can be seen, the slope of the reflected signal closely follows the glucose concentration.

Figure 2B:
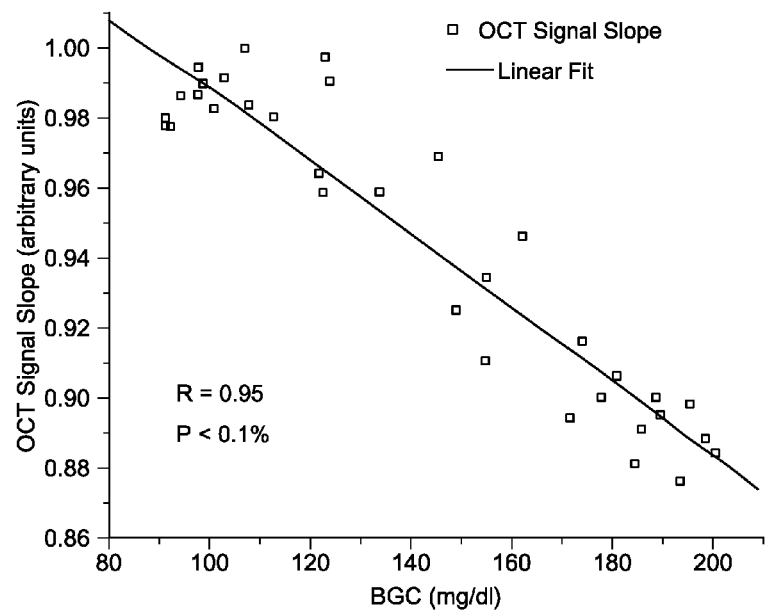

FIG. 2b illustrates the best-fit linear relation between the slope of the reflected optical signal in FIG. 2a with the measured blood glucose concentration. As can be seen, the slope of the reflected light in regions of blood-perfused tissue is highly correlated with glucose concentration. These data show a 0.95 correlation.

Applicant has determined that the information contained in scattered optical signals can be used to measure glucose concentration without creating and analyzing images. At a wavelength of around 1.3 µm, the scattering coefficient, $\mu_s$, is several times larger than the absorption coefficient, $\mu_a$, and a simple linear fit to the logarithmic data will yield the scattering coefficients within the dermis layer. For blood-perfused regions, this scattering coefficient can be related to glucose concentration changes within the blood.

A non-invasive glucose monitor ideally overcomes three problems. First, the speckle (noise) should be overcome within a reasonable test time. Second, the effect of tissues other than blood-perfused tissues should be minimized, and third, as much blood-perfused tissue as possible should be analyzed. Applicant addresses these problems by continuously scanning a two-dimensional area of the tissue to be monitored (preferably the skin) while at the same time interferometrically scanning to different depths. The area scanning optionally combined with the multiple level depth scanning permits measurement of many different localized areas of blood-perfused tissue, minimizing the effect of speckle. Preferably, the light comprises at least two different wavelengths of light having measurably different absorption and scattering properties for glucose, blood, or other biological indicators of blood-perfused tissues. The two different wavelengths permit identification of which measurements are of blood-perfused tissues.

In some respects, the invention can be thought of as a modification of OCT from an imaging technique to a non-imaging technique. Since no image is formed, the collection optics and data processing are greatly simplified. In addition, the surface scanning is changed from stepwise linear scanning to continuous or near continuous two dimensional area scanning to more rapidly and effectively reduce speckle.

Adapting an OCT system to blood glucose sensing, instead of imaging, provides non-invasive glucose concentration monitoring of a human or animal subject, because the scattered optical signal data can be collected and processed more easily and the resulting data can be correlated linearly to the level of glucose. Additionally, continuous scanning of the incident light beam over a two-dimensional area on the skin surface, instead of the conventional one-dimensional straight line, markedly improves, signal stability while dramatically reducing the noise associated with tissue inhomogeneity. Advantageously an area in the general shape of a circle is scanned.

More specifically, the invention uses interferometry, preferably low coherence interferometry (LCI), to measure the glucose concentration of human or animal blood-perfused tissue. LCI can be effected with convenient low coherence light sources and provides advantageously small volumes of constructive interference ("regions of optical interaction") that can be used to localize readings to blood-perfused tissue. Beam focusing can be used to further localize the regions of optical interaction. LCI uses a standard interferometer illuminated by low coherence light sources. The interferometer can be any one of the standard forms, e.g. Michaelson, Mach-Zehnder, or the like. The light sources can be LEDs or SLEDs.

The invention is advantageously directed to measure the blood glucose concentration from tissue located in the dermis layer of the skin (3 of FIGS. 1a and 1b). In this layer, the rate at which the light intensity decays is a function of the scattering and absorption coefficients, $\mu_s$ and $\mu_a$, respectively. The location of the blood-perfused tissue in the skin varies from subject to subject. It is often found just below the dermis/epidermis junction (100-350 microns depth) and in a deep region below the skin surface (greater than 600 microns).

With low coherence sources, the interferogram is generated over a small volume whose position in the depth of the object can be determined via the phase of a reference beam. This, in turn, can be controlled by a phase shifter, such as a movable reference reflector, preferably a mirror. Thus, a high degree of localization of the measured scattering phenomena can be achieved. For example, for a typical light emitting diode (LED) operating at a 1.3 μm wavelength, a depth resolution of 10 μm is easily achieved in biological tissues. Typically in biological tissues, the scatter of the light occurs at the interface between the cell membrane and the fluid that surrounds the cell (i.e. blood or interstitial fluid). Measuring this scatter permits the glucose level to be determined, as by the linear fit shown in FIG. 2b.

Figure 3:
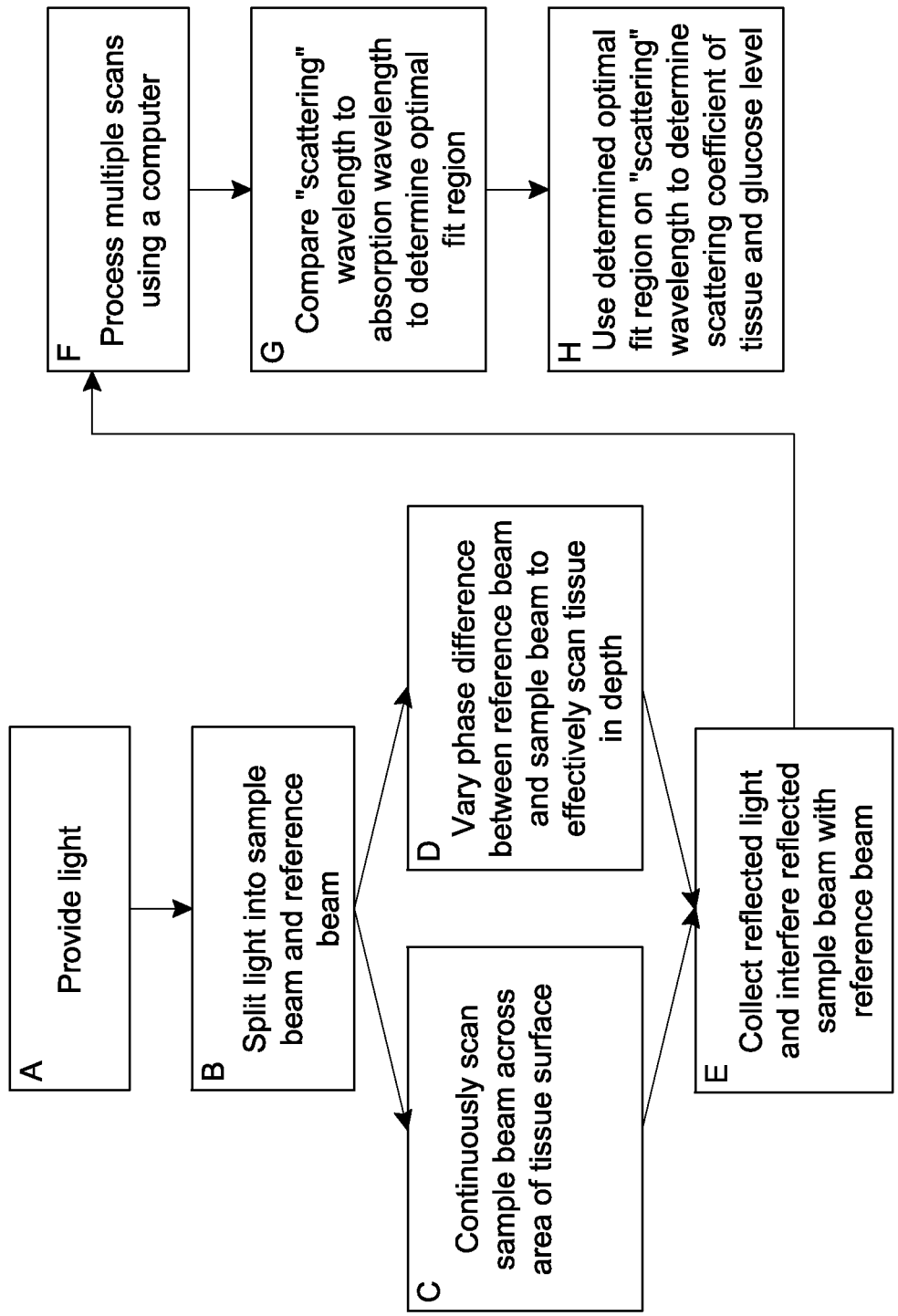
FIG. 3 is a schematic diagram illustrating a method of blood glucose monitoring in accordance with the invention.

FIG. 3 is a schematic block diagram of the method of measuring the blood glucose concentration on a human or animal subject. The first step, shown in Block A, is to provide light having scattering absorption or properties sensitive to glucose concentration within the tissue. Preferably the light provided comprises at least two different wavelengths. By different wavelengths is meant that the wavelengths should be sufficiently different that they have measurably different absorption and scatter properties for different levels of glucose and/or indicator components such as blood. Typically, the light is provided from multiple single wavelength sources, such as low coherence superluminescent diodes (SLEDs) at wavelengths in the red/near infrared range (RNIR). Alternatively, the light can be provided from a single broadband source appropriately notch filtered. Both wavelengths of light are advantageously directed in a single beam.

The next step, shown in Block B, is to split the single beam of light into a reference beam and a sample beam. The reference beam travels in an adjustable phase path denoted as the reference beam path (reference arm), and the sample beam travels in a sample beam path (sample arm) where it is directed onto the tissue to be monitored, e.g. the skin of a human diabetic. The light in the reference beam is directed over an adjustable phase path and will subsequently be interfered with sample light reflected from within the tissue.

In the third step, Block C, the sample beam is continuously or near continuously scanned over a two-dimensional area of the tissue while, at the same time, being interferometrically scanned in depth. Block D shows varying the phase (path length) of the reference beam so that light from the reference beam constructively interferes with reflected sample light from successively different depths of tissue. Block E shows the reflected light collected and interfered with the reference beam. As the interferometer sweeps in depth, the surface scan is also sweeping continuously. This "smears" out the scan and reduces the effect of speckle.

The next steps, Blocks F, G, and H are to process the resulting data to calculate glucose concentration. In essence, this is achieved by computing the scattering coefficient of glucose-containing tissue. Block F indicates the scanning data is input into a digital processor. Block G, which is optional, but advantageous, is to identify those scattering measurements that are from blood-perfused tissue (in or near blood vessels). Such identification can be accomplished, for example, by providing light of two different wavelengths, at least one of which scatters from blood-perfused tissues in a characteristic manner. Finally, in Block H, the scattering coefficient of the glucose containing tissue is calculated, and the correlated glucose level in blood is determined.

Figure 4:
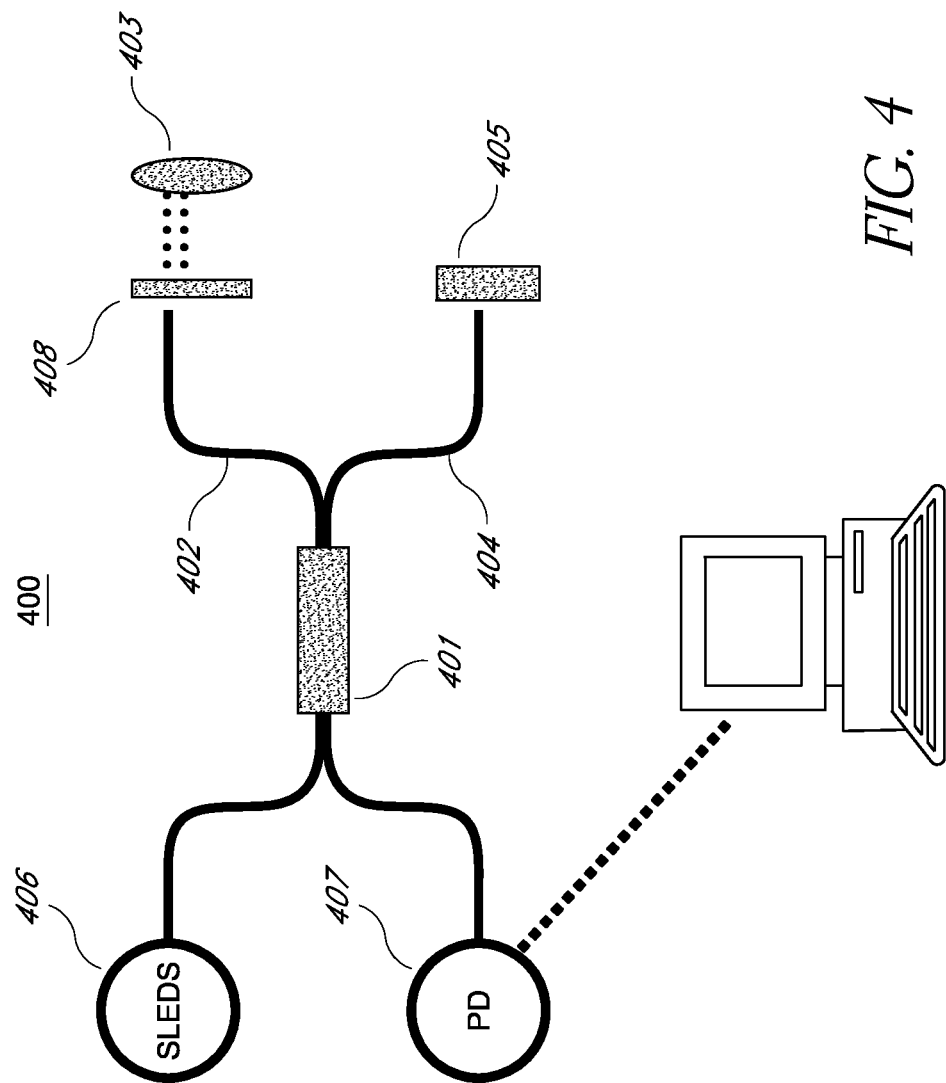
FIG. 4 schematically illustrates an apparatus useful for practicing the method of FIG. 3.

FIG. 4 schematically shows advantageous apparatus 400 for practicing the method of FIG. 3. The apparatus 400 comprises a fiber optics based low coherence interferometer (LCI). A 2×2 fiber optic, splitter 401 forms the basic interferometer. An optical input from light sources 406 is split between a sample beam 402 and a reference beam 404. Sample light in beam 402 is continuously scanned across a sample surface by scanner 408. Preferably, the end of the sample beam 402 can contain imaging optics 403 to tailor the spot size according to the area tissue being measured. Reference beam 404 is varied or adjusted in phase as by a moveable mirror 405 which can be vibrated or oscillated to scan depth. Reflected signals from beams 402 and 404 interfere and are presented to photodetector 407 for measurement. Advantageously, imaging optics 403 can provide high coupling efficiency between the optical system and the tissue.

The tissue volume with which the light interacts (referred to as the interaction volume) is determined by the spot size of the imaging optics (surface area) and the coherence length of the light (depth) The reference beam 404 has a scanning reflector 405 (such as a mirror). The reflector 405 of the interferometer determines the phase shift applied to the reference beam 404 and thus, which reflected light from the reference beam 404 will constructively interfere with the reflected sample beam 403. The differences in phase of the beams determines the depth from which scattered light will be measured. This can permit a fixed depth, adjustable depth, or a scan of multiple depths within the tissue. LCI is thus sensitive to the intensity of the reflected light localized in a small volume of tissue. Determination of the depth and interaction volume permits a more accurate selection of regions of blood-perfused tissue beneath the skin.

A photodetector 407 (such as a photodiode) can be used to measure the interference of the light from both the sample beam 402 and the reference beam 404. One or more photodetectors 407 may be used along with optical filters (not shown) designed for each of the different wavelength light sources 406 used in the measurement.

Preferably, the imaging optics 403 are beam focusing optics to reduce the beam cross section so as to minimize the region of optical interaction with the tissue. The use of these optics will enhance the selectivity of the signal while also reducing the effect of speckle.

Light passing through turbid biological tissue is subject to wavefront distortion that produces coherent noise or "speckle". The effect of speckle can be reduced by taking multiple scans from different locations on the tissue and then averaging these scans. This solution is impractical for the typical OCT imaging system, because the vast number of scans needed to reduce speckle would take too long and would produce a severe loss in the resolution of the image. However, for the present invention, the collection optics can be simpler. The present non-imaging system presents a practical solution to reducing coherent noise. Not only does the speckle effect significantly decrease, but the non-imaging system can continuously scan a two-dimensional area of tissue instead of being limited to a single scanning line. Area scans reduce speckle due to the diversity of tissue regions encompassed in the scan. They also maximize the coverage of blood-perfused tissue. Thus, coherent noise is also further reduced.

An alternative solution is to use parallel optical processing where multiple spots on the subject tissue are measured together to create "boiling" speckle. Boiling speckle occurs where the sub-spot speckle is changing so quickly that the observed speckle is averaged out by the human eye, or the integration time of the optical receiver. This inventive system may be modified to create boiling speckle by replacing the scanner 408 with either a lenslet array or a diffractive optical element (DOE). If the lenslet or DOE is rapidly translated or rotated about the optical axis at a very high speed, the observed speckle will be averaged out. Additionally, such a system reduces the number of scans required due to the greater variety of speckle detected.

Since glucose is delivered to the interstitial fluid (IF) in skin via blood, determining the scatter coefficient in the dermis layer of the tissue, where blood vessels are plentiful, provides the closest correlation to variations in glucose concentration. Again, an area scan increases the volume of blood-perfused tissue measured.

Area scanning could be achieved by a pair of rotating prisms that continuously move a sample beam spot over a circular area of the tissue surface. Advantageously, the spot would move a minimum of one spot diameter for each depth scan. Thus if the beam spot size is 12 microns and the depth scan is at a rate of 20 Hz, then the spot should advantageously be moved at a minimum rate of 240 microns per second and preferably much faster.

Spot diameters are typically in the range from about 10 microns to 100 microns and preferably 20 microns and higher.

The minimum area of the scan is defined by the number of spot diameters needed to move at the minimum depth scan rate. For the 12 micron spot and 20 Hz depth scan, the minimum area that would need scanning is about 2200 square microns, corresponding to a circular area of about 500 micron diameter. More preferably the system would be designed to cover an area corresponding to a diameter of 500 microns to 10,000 microns.

For speckle reduction using the boiling speckle method of noise reduction, the multiple spots would need to be moved quite rapidly. The spot should move at a minimum of one spot diameter in the integration time of the receiver. For individual spot sizes of about 10 microns and an integration time of about 4 microseconds, the spots would need to move at a minimum of $2.4 \times 10^5$ microns/sec.

The light sources 406 can be light emitting diodes (LED) or super luminescent diodes (SLEDs), both of which are semiconductor based light emitters whose wavelengths can be chosen to give the best contrast between absorption and scatter of blood and other biological constituents, such as water. Typically these wavelengths are in the red/near infrared (RNIR) region of the spectrum, however, longer and shorter wavelengths can be used for enhanced sensitivity. For the glucose measurements, two or more light sources are advantageous and can share the same optical paths through the interferometer.

One of the wavelengths can be chosen to have minimum absorption compared to the scattering coefficient for water and blood constituents. If the other wavelength is chosen to have peak absorption for certain biological constituents, then the difference in light attenuation between the two wavelengths can indicate the position in depth of a relevant structure, such as a blood vessel. Light from the two wavelengths is differently absorbed by the different constituents. This differential absorption differentially reduces the intensity of the scattered (reflected) light. Light reflected off the cellular membrane is partially absorbed by the respective constituent for that wavelength. Where the term "light is reflected from the blood" is used, it is understood to refer to light reflected from the cells in and around the blood vessels, and the constituent in the blood absorbs some of the light according to the specific wavelength and glucose level of the blood. These differences in the scattering and absorption properties provide for an optimal correlation between the scattered signal and blood glucose data.

One exemplary application is a first wavelength of about 1310 nm and a second wavelength of about 820-960 nm. A first wavelength of 1310 nm is chosen because the scattering properties of water and blood and blood constituents is at a maximum compared to the absorption properties of these fluids. The second wavelength, 820-960 nm, is chosen because the absorption of light is very high in the presence of hemoglobin, a blood constituent, (compared to the first wavelength). If the signal of the second wavelength were to experience a rapid decrease at a particular depth in the interaction volume, this rapid decrease would indicate the presence of hemoglobin, and hence, the location of blood-perfused tissue. It would thus indicate an optimal slope region for the scattering data of the first wavelength to be related to the glucose concentration.

A second example would be a first wavelength of about 1310 nm and a second wavelength of about 1450 nm. At this second wavelength, the scattering coefficients for blood and water are similar to those of the first wavelength. However, the absorption coefficient for water at this second wavelength is exponentially larger than that of the first wavelength. Thus, a differential measurement between these two wavelengths indicates changes in the hydration level of the tissue. Such changes can then be used to indicate an optimal slope region for measuring blood glucose. However, the use of these two specific wavelengths provides an additional benefit of sensor calibration. As the hydration level in the dermis layer varies, the scattering coefficient of the first wavelength may drift, even though the glucose concentration remains static. Thus, by measuring the skin hydration using the second wavelength, this drift can be compensated for and the OCT sensor can maintain calibration.

An exemplary analysis of the data to determine glucose level essentially involves the following steps:

1. Expressing the reflected intensity $I_r$ and the incident intensity $I_O$ as logarithms, e.g. $Ln(I_r)$, $Ln(I_O)$.
2. Plotting the logarithmic data in accordance with the scattering equation. Since the data at the 1310 nanometer wavelength is dominated by scattering (with minimal absorption) the logarithmic scattering equation can be approximated by $Ln(I_r) = L_n(I_O) - (\mu_t)(d)$ Where $\mu_t$ is the scattering coefficient and d is the depth of the scan.
3. Determining $\mu_t$ by regression analysis. This can be achieved by a linear regression through the logarithmic data to determine the best fit slope ($\mu_t$). Since, however, the glucose concentration is most accurately read in blood/IF, the regression should analysis is preferably selectively applied to those data points whose depth (or two-wavelength scattering characteristics) are indicative of blood/IF. The glucose concentration, as noted in connection with FIG. 2*b* above, at such is regions strongly correlated with the scattering coefficient $\mu_t$ and can readily calibrated to it.

This, or comparable algorithms can be readily implemented in digital processors by those skilled in the art to provide a rapid, non-invasive readout of glucose level.

It is understood that the above-described embodiments are illustrative of only a few of the many possible specific embodiments, which can represent applications of the invention. Numerous and varied other arrangements can be made by those skilled in the art without departing from the spirit and scope of the invention.

What is claimed is:

1. An apparatus for non-invasively measuring blood constituent levels within biological tissue, the apparatus comprising:
    at least one light source for providing a sample beam and a reference beam, the at least one light source providing at least two wavelengths of light, the at least one light source configured to direct the sample beam to the biological tissue, the at least two wavelengths of light including first and second wavelengths of light, the first wavelength of light having measurably different scattering properties sensitive to a first blood constituent relative to the second wavelength of light;

a phase shifter configured to adjust phase path of the reference beam;

a scanner configured to scan the sample beam over an area of the subject's tissue;

an interferometer that allows comparison of a reflected sample beam from the subject tissue with the reference beam;

at least one photodetector configured to generate non-image measurements from the reference beam and the reflected sample beam, the non-image measurements including at least scatter measurements of the first and second wavelengths of light; and blood constituent monitor configured to receive the non-image measurements and calculate, based on the non-image measurements, a level of a first blood constituent based at least partly on the scatter measurements of the first wavelength of light obtained at a location in the biological tissue where the scatter measurements of the second wavelength of light indicate a presence of blood-perfused tissue.

2. The apparatus of claim 1 further comprising:
a beam splitter to split light from the at least one light source into the sample beam and the reference beam;
wherein the phase shifter is configured to direct the reference beam to interfere with the reflected sample beam.

3. The apparatus of claim 1, wherein the scanner is configured to continuously scan a two-dimensional area of the biological tissue.

4. The apparatus of claim 1 wherein the scanner comprises a rapidly movable lens array or a rapidly movable diffractive optical element.

5. A system for non-invasively monitoring blood constituent level within biological tissue, the system comprising:
one or more processors configured to:
initiate scanning by an interferometric sensor of an area of biological tissue with light including first and second wavelengths, the first wavelength of light having measurably different scattering properties sensitive to a first blood constituent relative to the second wavelength of light;
receive non-image measurements from the interferometric sensor for at least one tissue depth, the non-image measurements including at least scatter measurements of the first and second wavelengths of light at the at least one tissue depth; and
in response to determining, based on the scatter measurements of the second wavelength of light at the at least one tissue depth, a tissue location indicative of a presence of blood-perfused tissue, determine a level of the first blood constituent within the biological tissue based at least partly on the scatter measurements of the first wavelength of light obtained at the tissue location.

6. The system of claim 5, wherein the one or more processors are configured to cause the interferometric sensor to provide the light from one or more light sources, wherein the light is split into a sample beam and a reference beam.

7. The system of claim 5, wherein the one or more processors are configured to cause the interferometric sensor to continuously scan the light over a two-dimensional area of the biological tissue.

8. The system of claim 5, further comprising the interferometer sensor.

9. The system of claim 8, wherein the interferometric sensor is an optical coherence tomography (OCT) sensor.

10. The system of claim 8, wherein the interferometric sensor includes a first wavelength and a second wavelength source, the first wavelength source configured to produce the first wavelength and the second wavelength source configured to produce the second wavelength, the first wavelength having measurably different scattering properties for hemoglobin-containing tissue or indicators of such tissue relative to the second wavelength.

11. The system of claim 5, wherein the interferometric sensor includes multiple wavelength sources, including wavelength sources for at least infrared light and near infrared light.

12. The system of claim 5, wherein the first blood constituent comprises hemoglobin.

13. The system of claim 5, wherein the first blood constituent comprises glucose.

14. A method for non-invasively monitoring blood constituent level within biological tissue, the method comprising:
initiating scanning by an interferometric sensor of an area of biological tissue with light including first and second wavelengths, the first wavelength of light having measurably different scattering properties sensitive to a first blood constituent relative to the second wavelength of light;
receiving light measurements from the interferometric sensor for at least one tissue depth, the light measurements including at least scatter measurements of the first and second wavelengths of light at the at least one tissue depth; and
without generating an image from the light measurements and in response to determining, based on the scatter measurements of the second wavelength of light at the at least one tissue depth, a tissue location indicative of a presence of blood-perfused tissue, determining a level of the first blood constituent within the biological tissue based at least partly on the scatter measurements of the first wavelength of light obtained at the tissue location.

15. The method of claim 14, wherein said initiating scanning by the interferometric sensor comprises causing the interferometric sensor to provide the light from one or more light sources, wherein the light is split into a sample beam and a reference beam.

16. The method of claim 15, further comprising varying phase of the reference beam and causing a reflected portion of the sample beam to interfere with the reference beam.

17. The method of claim 15, further comprising adjusting the reference beam to constructively interfere with reflected light from a selected depth within the biological tissue.

18. The method of claim 14, wherein said initiating scanning by the interferometric sensor comprises causing the interferometric sensor to continuously scan the sample beam over a two-dimensional area of the biological tissue.

19. The method of claim 14, wherein the interferometric sensor includes a first wavelength and a second wavelength source, the first wavelength source configured to produce the first wavelength of light and the second wavelength source configured to produce the second wavelength of light.

20. The method of claim 19, wherein the first wavelength source and second wavelength source produce wavelengths at about 1310 nm and at about 1450 nm, respectively.

21. The method of claim 19, wherein at least one of the first and second wavelength sources produce wavelengths within a range from 820 nm to 960 nm.

22. The method of claim 14, wherein the first blood constituent comprises hemoglobin.

* * * * *

UNITED STATES PATENT AND TRADEMARK OFFICE
CERTIFICATE OF CORRECTION

| | |
|---|---|
| PATENT NO. | : 8,788,003 B2 |
| APPLICATION NO. | : 13/456137 |
| DATED | : July 22, 2014 |
| INVENTOR(S) | : Matthew J. Schurman |

It is certified that error appears in the above-identified patent and that said Letters Patent is hereby corrected as shown below:

On the Title Page

Page 1 (item 57, Abstract) at lines 13-14, change "blood-profused" to --blood-perfused--.

In column 1 (page 5, item 56) at line 54, Under Other Publications, change "Opthalmol," to --Ophthalmol,--.

In column 1 (page 5, item 56) at line 55, Under Other Publications, change "Attentuation" to --Attenuation--.

In column 1 (page 5, item 56) at line 57, Under Other Publications, change "Phvs." to --Phys.--.

In column 1 (page 5, item 56) at line 61, Under Other Publications, change "Phvs." to --Phys.--.

In column 1 (page 5, item 56) at line 67, Under Other Publications, change "Phvs." to --Phys.--.

In column 1 (page 5, item 56) at line 68, Under Other Publications, change "Phvs." to --Phys.--.

In column 2 (page 5, item 56) at line 32, Under Other Publications, change "Chern." to --Chem.--.

In column 2 (page 5, item 56) at line 51, Under Other Publications, change "CoherenceTomography,"" to --Coherence Tomography,"--.

In column 2 (page 5, item 56) at line 66, Under Other Publications, change "Artlf." to --Artif.--.

In column 1 (page 6, item 56) at line 30, Under Other Publications, change "Reflectrometrv,"" to --Reflectometry,"--.

Signed and Sealed this
Third Day of March, 2015

Michelle K. Lee
*Deputy Director of the United States Patent and Trademark Office*

In column 2 (page 6, item 56) at line 11, Under Other Publications, change "Chern." to --Chem.--.

In column 2 (page 6, item 56) at line 25, Under Other Publications, change "Surq." to --Surg.--.

In the Specification

In column 3 at line 42, Change "IF blood-perfused tissues)" to --IF (blood-perfused tissues)--.